United States Patent [19]

Vacanti et al.

[11] Patent Number: 5,770,193

[45] Date of Patent: *Jun. 23, 1998

[54] PREPARATION OF THREE-DIMENSIONAL FIBROUS SCAFFOLD FOR ATTACHING CELLS TO PRODUCE VASCULARIZED TISSUE IN VIVO

[75] Inventors: Joseph P. Vacanti, Winchester; Robert S. Langer, Somerville, both of Mass.

[73] Assignee: Massachusetts Institute of Technology Children's Medical Center Corporation, Cambridge, Mass.

[*] Notice: The term of this patent shall not extend beyond the expiration date of Pat. No. 5,567,612.

[21] Appl. No.: 203,521

[22] Filed: Feb. 28, 1994

Related U.S. Application Data

[63] Continuation of Ser. No. 401,640, Aug. 30, 1989, abandoned, which is a continuation of Ser. No. 933,018, Nov. 20, 1986, abandoned.

[51] Int. Cl.$^6$ .............................. C12N 11/08; C12N 5/00; A61F 2/28; A61F 2/18

[52] U.S. Cl. ..................... 424/93.7; 424/422; 424/426; 424/486; 424/548; 424/549; 435/177; 435/178; 435/180; 435/181; 435/395; 435/398; 435/402

[58] Field of Search .................................. 435/177, 180, 435/181, 182, 240.1, 240.23, 240.242, 240.243, 395, 398, 402; 424/422, 423, 426, 486, 93.7, 548, 549; 128/1 R; 524/24; 525/421; 436/823; 623/11, 12, 13

[56] References Cited

U.S. PATENT DOCUMENTS

| | | | |
|---|---|---|---|
| 3,883,393 | 5/1975 | Knazek et al. | 435/240.242 |
| 3,992,725 | 11/1976 | Homsy | 3/1 |
| 4,026,304 | 5/1977 | Levy | 128/419 |
| 4,060,081 | 11/1977 | Yannas et al. | 128/156 |
| 4,192,827 | 3/1980 | Mueller et al. | 525/123 |
| 4,239,664 | 12/1980 | Teng et al. | 260/17.4 R |
| 4,277,582 | 7/1981 | Mueller et al. | 525/421 |
| 4,280,954 | 7/1981 | Yannas et al. | 260/123.7 |
| 4,304,591 | 12/1981 | Mueller et al. | 71/93 |
| 4,328,204 | 5/1982 | Wasserman | 424/486 |
| 4,348,329 | 9/1982 | Chapman | 260/403 |
| 4,416,986 | 11/1983 | Markus et al. | 435/70.1 |
| 4,427,808 | 1/1984 | Stol et al. | 524/24 |
| 4,431,428 | 2/1984 | Schmer | 604/897 |
| 4,438,198 | 3/1984 | Schmer | 435/178 |
| 4,444,887 | 4/1984 | Hoffmann | 435/240 |
| 4,446,234 | 5/1984 | Russo et al. | 435/29 |
| 4,450,150 | 5/1984 | Sidman | 424/1.1 |
| 4,458,678 | 7/1984 | Yannas et al. | 435/240.1 |
| 4,485,096 | 11/1984 | Bell | 424/95 |
| 4,485,097 | 11/1984 | Bell | 424/95 |
| 4,489,056 | 12/1984 | Himmelstein | 424/486 |
| 4,505,266 | 3/1985 | Yannas et al. | 128/1 R |
| 4,520,821 | 6/1985 | Schmidt | 435/240.21 |
| 4,528,265 | 7/1985 | Becker | 435/172.1 |
| 4,544,516 | 10/1985 | Hughes et al. | 264/108 |
| 4,545,082 | 10/1985 | Hood | 623/12 |
| 4,553,272 | 11/1985 | Mears | 623/1 |
| 4,559,304 | 12/1985 | Kasai et al. | 435/240.43 |
| 4,563,490 | 1/1986 | Stol et al. | 524/24 |
| 4,576,608 | 3/1986 | Homsy | 623/13 |
| 4,609,551 | 9/1986 | Caplan et al. | 424/95 |
| 4,645,669 | 2/1987 | Reid | 435/240.23 |
| 4,713,070 | 12/1987 | Mano | 623/12 |
| 4,846,835 | 7/1989 | Grande | 623/11 |
| 4,891,225 | 1/1990 | Langer et al. | 424/428 |
| 4,963,489 | 10/1990 | Naughton et al. | 435/240.23 |
| 5,041,138 | 8/1991 | Vacanti et al. | 623/16 |
| 5,567,612 | 10/1996 | Vacanti et al. | 435/240.23 |

OTHER PUBLICATIONS

Thunoff et al Urology 21:155–158 1983.
Structure & Function in Man W B Saunders Co 1982, pp. 85–88, 383, 384, 413; 484 504–507.
Histology Larson et al W B Saunders Co 1976 pp. 86, 87 & 88.
Thüroff et al, "Culturing Rabbit Vesical Smooth Muscle Cells for Lining of Dissoluable Synthetic Prosthesis", Urology, V. 21(2), 155–158, 1983.
Vacanti, et al J Pediatric Surgery 23(1) 3–9 1988.
Leong, et al J Biomedical Materials Research 19:941–955.
Naji, et al Surgery 86(2) 218–226 1979.
Pimpl et al, Lagenbecks Archiv, 36215–36218, 1984.
Pimpl et al, Eur. Surg. Res. V. 19, 53–61, 1987.
Sasaki, Virchows Arch, V. 409, 325–334, 1986.
Sapoznikova et al, Biological Abstracts, V. 86, #76896, 1987.
Culliton Science 246:748 1989.
Thompson Science 258:744–746 1992.
Freshney *Animal Cell Culture: A Practical Approach* 1986 IRL Press pp. 179–180.

*Primary Examiner*—David M. Naff
*Attorney, Agent, or Firm*—Arnall Golden & Gregory, LLP

[57] ABSTRACT

Fibers of a biocompatible, biodegradable or non-biodegradable, synthetic polymer are provided, and are formed into a three-dimensional scaffold. The fibers of the scaffold may have a branched configuration extending outwardly from a central stem. The fibers provide sufficient surface area to permit attachment to the scaffold in vitro of an amount of cells effective to produce functional vascularized organ tissue in vivo. Fibers of the scaffold are spaced apart such that the maximum distance over which diffusion of nutrients and gases must occur through a mass of cells attached to the fibers is between 200 and 300 microns. The diffusion provides free exchange of nutrients, gases and waste to and from cells proliferating throughout the scaffold in an amount effective to maintain cell viability throughout the scaffold in the absence of vascularization. Cells derived from vascularized organ tissue are attached in vitro to the surface of the fibers uniformly throughout the scaffold and the cells are grown on the scaffold in a nutrient solution in vitro to form a cell-scaffold composition. Growth factors, compounds stimulating angiogenesis and immunomodulators may be provided in the cell-scaffold composition and the fibers may have a coating to enhance cell attachment. The cell-scaffold composition is implanted in a host at a location having adequate vascularization to allow growth of blood vessels into the cell-scaffold composition. Combinations of cell-scaffold compositions containing different cell populations may be implanted.

17 Claims, 7 Drawing Sheets

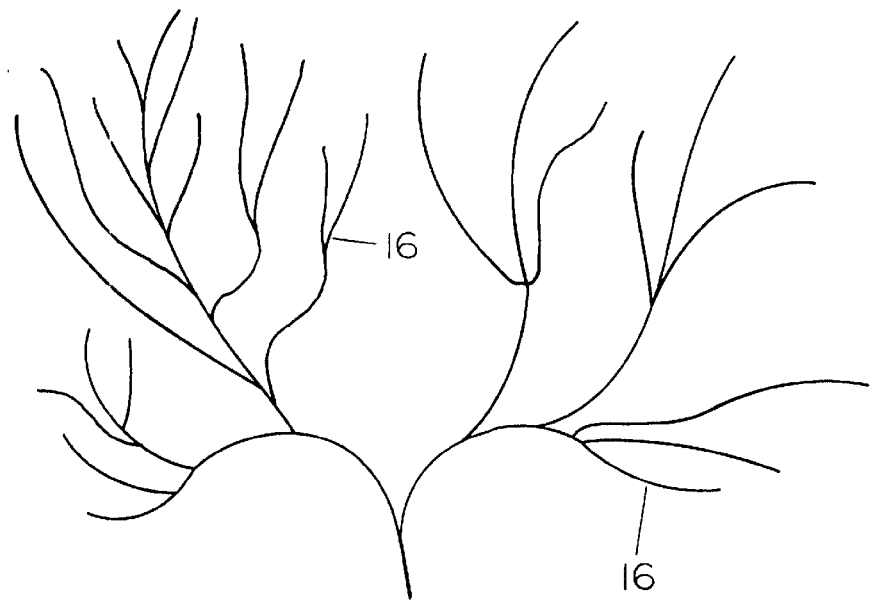
FIG.2
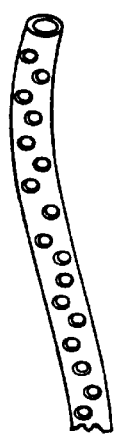 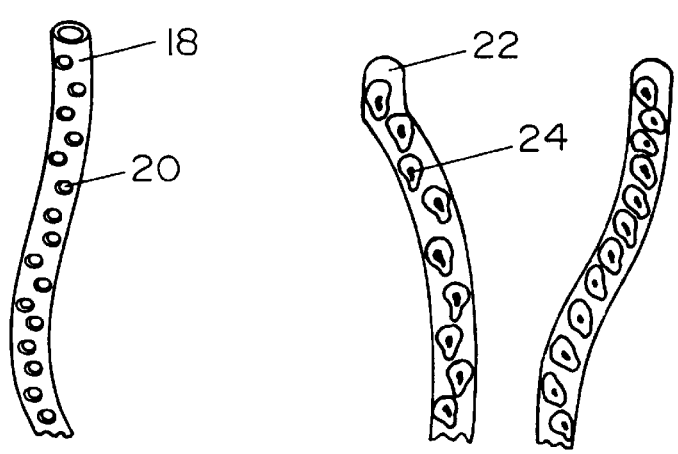
FIG.3A              FIG.3B

PREPARATION OF THREE-DIMENSIONAL FIBROUS SCAFFOLD FOR ATTACHING CELLS TO PRODUCE VASCULARIZED TISSUE IN VIVO

This is a continuation of U.S. patent Ser. No. 07/401,460 filed Aug. 30, 1989, now abandoned, which is a continuation of U.S. patent application Ser. No. 06/933,018 filed Nov. 20, 1986, now abandoned.

BACKGROUND OF THE INVENTION

This application is generally in the field of medicine and cell culture, and in particular in the area of implantable organs formed on bioabsorbable artificial matrices.

There are many diseases afflicting mankind which cause permanent destruction of vital organs and tissues. Loss of organ function can also result from congenital defects or injury. The long term success in restoring organ function has been limited.

One example of a disease causing loss of organ function is diabetes mellitus. Diabetes mellitus causes the destruction of beta cells of the pancreas which secrete the important polypeptide insulin. As a consequence, serum glucose levels rise to high values because glucose cannot enter cells to meet their metabolic demands. Through a complex series of events, major problems develop in all systems secondary to the vascular changes which occur. The current method of treatment consists of the exogenous administration of insulin, which results in imperfect control of blood sugar levels. The degree of success in averting the complications of diabetes remains controversial.

A recent and still experimental approach has been the transplantation of pancreatic tissue, either as a whole organ or as a segment of an organ, into the diabetic patient. Serum glucose appears to be controlled in a more physiological manner using this technique and the progression of complications is thereby slowed. Another approach has been the transplantation of islet cells through injection of isolated clusters of islet cells into the portal circulation, with implantation in the vascular bed of the liver. This method was attempted in the 1970s, but was not successful in achieving long-term benefits. More recent experimental methods have included encapsulation or binding to carrier beads of pancreatic beta cells to prevent immune attack by the host and injection of fetal beta cells beneath the capsule of the kidney.

There are also many diseases of the liver which cause significant scarring of the organ, with ultimate hepatic failure. There are no artificial support systems for liver failure, so that liver failure has always resulted in the death of the patient. Transplantation of the whole liver has become an increasingly successful surgical manipulation in the 1980's, largely through the efforts of Dr. Thomas Starzl. However, the technical complexity of the surgery, the enormous loss of blood, the stormy post-operative course, and the many unknowns of hepatic transplantation have made it an expensive technology available only in major medical centers. Donor scarcity, especially in the pediatric age group, has limited the number of patients with end-stage liver disease who can benefit from hepatic transplantation. the past, loss of the majority of intestine was a fatal condition. Patients can now be supported totally with nutrition supplied via the veins. This is thought of as a "half-way technology", however, because of the many complications associated with this technique. For example, over time many patients on total parenteral nutrition develop irreversible liver disease and die of their liver disease. Other patients develop severe blood stream infections requiring multiple removal and replacement procedures. They may eventually lose all available veins and succumb of malnutrition or die of infection.

Intestinal transplantation has been unsuccessful to date because of major biological problems. There are large numbers of lymphocytes in the intestine which are transferred to the recipient. These may produce an immunologic reaction termed "graft vs. host" disease.

Diseases of the heart are a major cause of disease and mortality in this country. Cardiac transplantation has been an increasingly successful technique where heart muscle has failed, but, as in the case of liver transplants, requires a donor and the use of strong immunosuppressant drugs.

Loss of skeletal and smooth muscle function can lead to deforming illnesses. Methods of muscle and nerve transfer have been developed by surgeons through the last fifty years which are Ingenious in design. An example of a recent technique for restoring nerve function has been to string dead nerve fibers from nerve centers to places with lost nerve function. Unfortunately, the results are often imperfect.

Loss, deformation or obstruction of blood vessels is another frequent cause of disease, such as high blood pressure or aneurysm. In the past, surgeons have primarily dealt with this problem by grafting blood vessels from another portion of the body to the affected area or by implanting cloth substitutes as permanent replacements. Disadvantages include the requirement of multiple surgery as well as the associated pain to the patient.

Skin is an organ subject to damage by disease or injury which performs a vital role in protecting the body from fluid loss and disease. Although skin grafts have been prepared form animal skin or the patient's skin, more recently "artificial skin" formed by culturing epidermal cells has been utilized. A number of patents have disclosed methods for forming artificial skin by seeding a fibrous lattice with epidermal cells. For example, U.S. Pat. No. 4,485,097 to Bell teaches a hydrated collagen lattice which, in combination with contractile agents such as platelets and fibroblasts and cells such as keratinocytes, is used to produce a skin-equivalent. U.S. Pat. No. 4,060,081 to Yannas et al. discloses a multilayer membrane useful as synthetic skin which is formed from an insoluble non-immunogenic material which is nondegradable in the presence of body fluids and enzymes, such as cross-linked composites of collagen and a mucopolysaccharide, overlaid with a non-toxic material such as a synthetic polymer for controlling the moisture flux of the overall membrane. U.S. Pat. No. 4,458,678 to Yannas et al. discloses a process for making a skin-equivalent material wherein a fibrous lattice formed from collagen cross-linked with glycosaminoglycan is seeded with epidermal cells.

A disadvantage to the first two methods is that the matrix is formed of a "permanent" synthetic polymer. The '678patent has a feature that neither of the two prior patents has, a biodegradable matrix which can be formed of any shape, using the appropriate cells to produce an organ such as the skin. Unfortunately, there is a lack of control over the composition and configuration of the latter matrices since they are primarily based on collagen. Further, since collagen is degraded by enzymatic action as well as over time by hydrolysis, the degradation is quite variable.

Although skin is considered to be an "organ" of the body, these methods for making artificial skin have not been used to make other types of organs such as a liver or pancreas, despite the broad claim that the disclosed or similar techniques could be utilized to do so. It is postulated that the cells within the center of the other organs tend to die after a period of time and that the initial growth rate is not maintained, in a manner analogous to the situation with very large tumors which are internally necrotic. This result is probably due to a decrease in diffusion of nutrients into the growing threedimensional structure as the cell density and thickness increase.

It is therefore an object of the present invention to provide a method and means for providing a variety of organs, including skin, liver, kidneys, blood vessels, nerves, and muscles which functionally resemble the naturally occurring organ.

It is a further object of the present invention to provide a method for designing, constructing and utilizing artificial matrices as temporary scaffolding for cellular growth and implantation.

It is a still further object of the invention to provide biodegradable, non-toxic matrices which can be utilized for cell growth, both in vitro and in vivo as support structures in transplant organs immediately following implantation.

It is another object of the present invention, to provide a method for configuring and constructing biodegradable artificial matrices such that they not only provide a support for cell growth but allow and enhance vascularization of the growing cell mass following implantation.

It is yet another object of the invention to provide matrices in different configurations so that cell behavior and interaction with other cells, cell substrates, and molecular signals can be studied in vitro.

SUMMARY OF THE INVENTION

The present invention is a technique whereby functional cells from a needed organ are grown on polymer scaffolding using cell culture techniques followed by transfer of the polymer-cell scaffold into a patient at a site appropriate for attachment, growth and function, after attachment and equilibration. Success depends on the ability of the implanted cells to attach to the surrounding environment and to stimulate angiogenesis. Nutrients and growth factors are supplied during cell culture allowing for attachment, survival or growth as needed. Once the structure is implanted and vascularization takes place, the resulting organoid is a true chimera formed of parenchymal elements of the donated tissue and vascular and matrix elements of the host. Vascular ingrowth following implantation allows for normal feedback mechanisms controlling the soluble products of the implanted cells.

The preferred material for forming the matrix or support structure is a biodegradable artificial polymer which is degraded by hydrolysis at a controlled rate and resorbed. The materials provide the maximum control of degradability, manageability, size, and configuration. Two configurations for organ structures are presently preferred: a branched fibrous tree-like structure and a flat disc configured to form attachment points for cells. Theoretical calculations of the maximum cell attachment suggest that a disc one centimeter in diameter allows for attachment of 200,000 cells. Branching fibers, 30 microns in diameter and one centimeter in length, can support 125,000,000 cells and provides even greater access of nutrients to the cells. Other compounds may be incorporated into the biodegradable matrix which enhance ingrowth of blood vessels following implantation. Nutrients, growth factors, inducers of differentiation or de-differentiation, products of secretion, immunomodulators, inhibitors of inflammation, regression factors, biologically active compounds which enhance or allow ingrowth of the lymphatic network or nerve fibers, and drugs can also be incorporated into the matrix or provided in conjunction with the matrix, in solution or incorporated into a second biodegradable polymer matrix.

A number of cells may be grown on these matrices, with the matrix constructed for optimal growth of that particular type of cell. Examples of cells which are suitable for implantation include hepatocytes and bile duct cells, islet cells of the pancreas, parathyroid cells, thyroid cells, cells of the adrenal-hypothalmic-pituitary axis including hormone-producing gonadal cells, epithelial cells, nerve cells, heart muscle cells, blood vessel cells, lymphatic vessel cells, kidney cells, and intestinal cells, cells having formed bone, cells forming cartilage, cells forming smooth muscle and cells forming skeletal muscle.

Growing the cells in culture allows manipulation of the cells which may be beneficial following implantation of the matrix cell structure. Possible manipulation includes the introduction of genes into the cells to make proteins which would otherwise be absent, such as those resulting from liver protein deficiencies and metabolic defects such as cystic fibrosis. Repression of gene expression may also be used to modify antigen, expression on the cell surface, and thereby the immune response, so that cells are not recognized as foreign.

The present invention also provides techniques and matrices for in vitro studies. Although current methods of cell culture have provided valuable insight into fundamental aspects of cell organization and function, studies of cell behavior, communication, control, and morphogenesis have been difficult for lack of a system controllable in three dimensions. Artificial matrices which have been coated with attached cells can be embedded in extracellular matrices such as collagen, basement membrane complexes such as Matrigel™, or other materials. Various combinations of cell types, biochemical signals for growth, differentiation, migration, and various extracellular matrix components may then be examined in vitro in a three-dimensional system. By controlling all of these elements, and watching behavior, the field of biomedical science may gain new insights into the actions of cells in a setting more closely resembling structure as it occurs in nature.

BRIEF DESCRIPTION OF THE DRAWINGS

FIG. 2 is a plan drawing of a branched fibrous structure for use as a cell matrix.

FIGS. 3A and 3B are perspective drawings of fibers used in the branch structure of FIG. 2, (3A) hollow fibers with pores and (3B) solid fibers seeded with cells.

DETAILED DESCRIPTION OF THE INVENTION

Figure 1A:
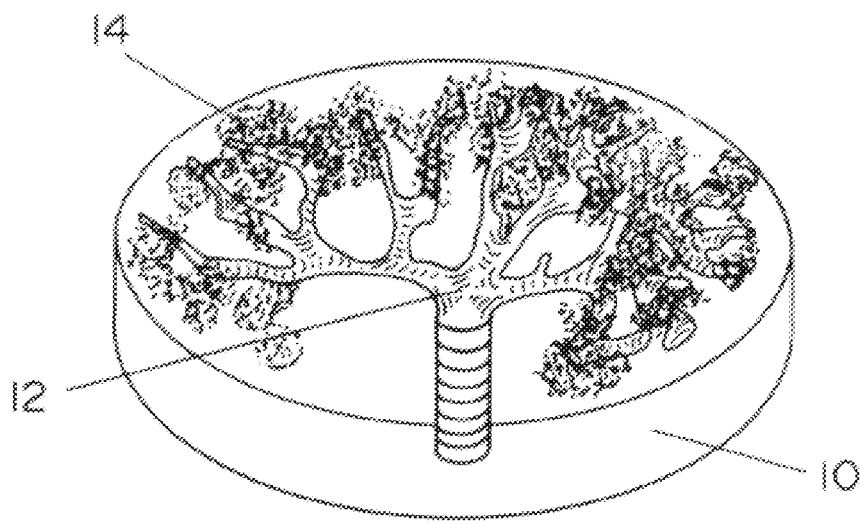
FIG. 1A is a perspective drawing of a polyanhydride polymer disc seeded with cells.

The present invention is a method to provide functional organ equivalents using bioabsorbable artificial substrates as temporary scaffolding for cellular transfer and implantation. The success of the method depends on the integration of the following principles:

1. Every structure in living organisms is in a dynamic state of equilibrium, undergoing constant renewal, remodeling and replacement of functional tissue which varies from organ to organ and structure to structure.
2. Dissociated structural cells tend to reform structure, depending on the environment in which they are placed and the degree of alteration which they have undergone.
3. Dissociated cells placed in mature tissue remodel the mature tissue only to a limited extent.
4. Tissue cannot be implanted in volumes greater than two to three mm³, because nutrition is supplied by diffusion until new blood vessels form, and this distance is the maximum diffusion distance.

The latter principle is a key point in the configuration of the support matrices. For an organ to be constructed in tissue culture and subsequently successfully implanted, the matrices must have sufficient surface area and exposure to nutrients such that cellular growth and differentiation can occur prior to the ingrowth of blood vessels following implantation. After implantation, the configuration must allow for diffusion of nutrients and waste products and for continued blood vessel ingrowth as cell proliferation occurs.

This method for replacing or supplementing lost organ function has a number of advantages over either pharmacologic manipulation or transplantation of whole organs or parts of organs. Although great strides have been made in these areas, the results of these efforts are-often imperfect. Success in transplantation or pharmacologic manipulation may modify the outcome of a disease, but it usually does not result in cure, or it trades the original disease for the complications of non-specific immunosuppression.

For example, an advantage of the present method is that it provides a means for selective transplantation of parenchymal cells which possess the necessary biologic function, without transplantation of passenger leucocytes and antigen-presenting cells. The result is a greatly reduced risk of rejection of tissue without the use of drugs, especially if one is able to culture cells of the same or similar HLA tissue type. The present invention has another advantage over other means for treating organ function loss since the cells may be manipulated while in culture to introduce new genes to make absent protein products or they may be modified to repress antigen expression on the cell surfaces-so that immunosuppression is not needed when cells of the same HLA tissue type are not available.

The prospect of culturing the recipient's own cells for implantation has a further advantage: the elimination of the need for organ donors. For example, if a patient has lost 90% of his intestine because of ischemic damage, cells from the remaining 10% can be harvested and cultured. The cells expand in a logarithmic fashion in culture. The cells are cultured until suitable numbers of cells are achieved, the cells are grown onto appropriate polymer scaffold, and placed back into the patient, to be allowed to vascularize, grow and function as a neointestine.

In distinct contrast to the prior art, the present method for controlled implantation of functional cells into patients using polymers as temporary scaffolding produces an organ which is vascularized in vivo to allow growth of the cells in a three-dimensional configuration similar to that of the organ whose function they are replacing. Both the design and construction of the scaffolding, as well as the conditions of the initial cell culture, are used to encourage cells to achieve their biological potential and replicate the ontogeny of organ formation which occurs in embryonic and fetal life. This new technique is termed chimeric neomorphogenesis.

The design and construction of the scaffolding is of primary importance. The matrix should be shaped to maximize surface area to allow adequate diffusion of nutrients and growth factors to the cells. The maximum distance over which adequate diffusion through densely packed cells can occur appears to be in the range of approximately 200 to 300 microns under conditions similar to those which occur in the body, wherein nutrients and oxygen diffuse from blood vessels into the surrounding tissue.

In the present invention, the cells are initially cultured using techniques known to those skilled in the art of tissue culture. However, once the cells have begun to grow and cover the matrix, they are implanted in a patient at a site appropriate for attachment, growth and function. One of the advantages of a biodegradable polymeric matrix is that angiogenic compounds may be incorporated directly into the matrix so that they are slowly released as the matrix degrades in vivo. As the cell-polymer structure is vascularized and the structure degrades, the cells will differentiate according to their inherent characteristics. For example, cells which would normally form tubules within the body will shape themselves into structures resembling tubules and nerve cells will extend along an appropriately constructed pathway.

In the preferred embodiment, the matrix is formed of a bioabsorbable, or biodegradable, synthetic polymer such as a polyanhydride, polyorthoester, or polyglycolic acid, alone or coated with extracellular components such as collagen, fibronectin, laminin, and complex mixtures of the above such as basement membrane Matrigel™. Other polymer materials can be used, depending on the ultimate disposition of the growing cells, including polymethacrylate, silicon polymers, and other non-biodegradable materials. A non-degradable material is particularly useful when the cells are grown in culture for purposes other than transplantation since the preferred matrix structure allows for a higher immobilized cell density than can normally be achieved where nutrients are supplied solely by diffusion. This matrix structure allows the in vitro study of various types of cells in combination, biochemical signals for growth, differentiation, migration and various extracellular matrix components. These studies are particularly useful in understanding cell to cell interaction: behavior, communication, control, and morphogenesis.

Figure 1B:
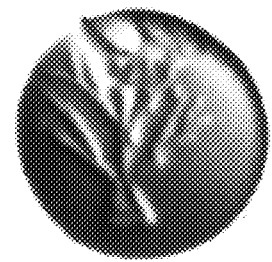
FIG. 1B is a photomicrograph of the disc of FIG. 1A seeded with hepatocytes.

The polymer structure must be appropriate for the size of the cell to be implanted, as well as to maximize the cell's exposure to the surrounding environment. It must also be designed to enhance the cell's ability to "call in" blood vessels. Examples of presently preferred structures are shown in FIGS. 1A and 1B, and FIG. 2. In FIG. 1A, a contoured polyanhydride disc 10, 1.0 cm in diameter, is used to support monolayer cell growth. The surface of the disc is configured to form a branching structure 12 for seeding of cells such as hepatocytes 14. FIG. 1B is a phase-contrast photo-micrograph of a branch point in the polymer which demonstrates the attachment of the hepatocytes to the polymer.

A disc 1.0 cm in diameter allows for attachment of approximately 200,000 cells. The branching fibers 16 shown in FIG. 2, 30 microns in diameter and 1.0 cm in length, can support 125,000,000 cells, roughly a five-hundred fold increase over the number of cells which can attach to the disc shown in FIG. 1A. As shown in FIG. 3A and FIG. 3B, the fibers 16 used to make the structure in FIG. 2 may be hollow fibers 18 with pores 20 of a size appropriate for the type of cell to be seeded, or solid fibers 22 of a material with an appropriate outer surface for the attachment of the desired cells 24.

According to the present invention, the structure or scaffold, such as the one shown in FIG. 2, is placed in tissue culture with the appropriate cell populations. In an example in which a liver organ is constructed, the cell populations include hepatocytes, and bile duct cells. Cells may be derived from the host, a related donor or from established cell lines. Fetal cell lines may be utilized since these cells are generally more hardy than other cell lines.

In a variation of the method using a single matrix for attachment of one or more cell lines, the scaffolding is constructed such that initial cell attachment and growth occur separately for each population. A unitary scaffolding may also be formed of different materials to optimize attachment of various types of cells. Attachment is a function of both the cell and structure composition. For example, overlaying collagen on a material such as a polyanhydride can increase adhesion of cells such as hepatocytes. In one example, long, solid fibers are seeded with blood vessel endothelial cells for insertion into a structure seeded with kidney cells. After implantation and degradation of the polymer, the blood vessel cells form the appropriate connections for delivery of the blood to the desired locations. Ducts for excretion by the organ may be constructed in an analogous manner, always taking advantage of the inherent behavior of the cells. Ingrowth of the lymphatic network and nerve fibers may also be encouraged.

Although the presently preferred embodiment is to utilize a unitary matrix structure implanted into a host, there are situations where it may be desirable to use multiple cell-matrix structures, implanted in locations at the most optimum time for growth of the attached cells to form a functioning three-dimensional organ structure from the different cell-matrix structures. Alternatively, it may be desirable to prepare the implantation site by initially exposing the cells at the site to a biodegradable polymer matrix including compounds or "de-differentiators" which induce a reversion of the surrounding mesenchymal cells to become more embryonic. The implanted cell matrix structure may then develop more normally in the fetal environment than it would surrounded by more mature cells.

Figure 4:
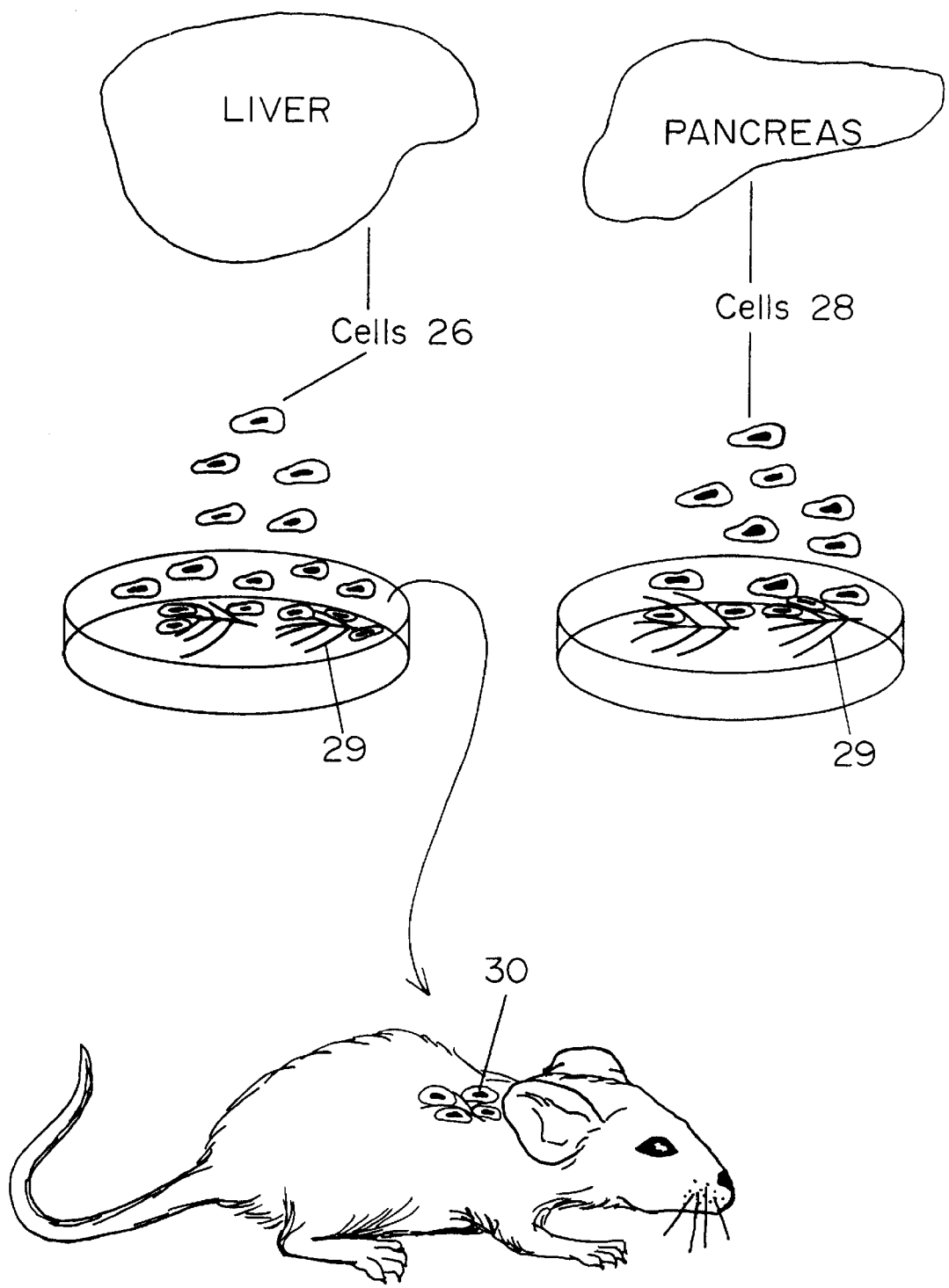
FIG. 4 is a schematic drawing of controlled cellular implantation according to the present invention using artificial bioabsorbable matrices seeded with liver or pancreas cells and implanted in a mouse.

As shown in FIG. 4, once the selected cells 26 or 28 have been seeded onto the branched polymer structure 29 and grown in tissue culture, the cell-polymer structure 30 is implanted in an appropriate location having adequate vascularization.

In one example of the invention, hepatocytes were incubated for four days in cell culture on polyorthoester discs (shown in FIG. 1B) and then implanted into rats which had undergone a partial hepatomectomy. The animals were sacrificed seven days later. One animal had developed a small nodule of hepatocytes surrounded by a foreign-body reaction in the area of the implanted disc. The nodule was vascularized and contained healthy hepatocytes, two of which were undergoing active cell division.

Figure 5A:
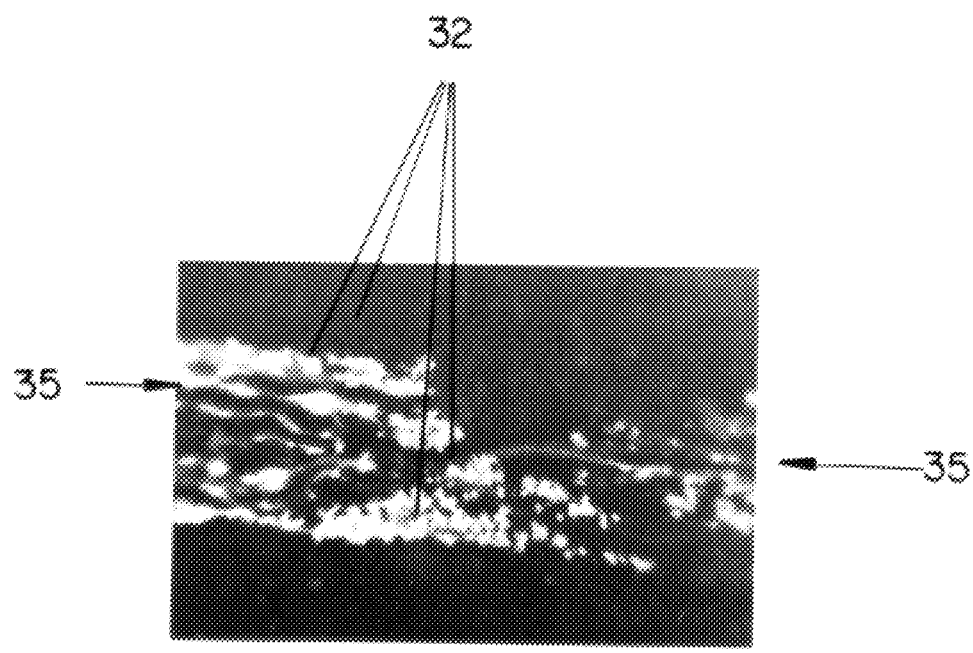
FIGS. 5A and 5B are photographs of liver cells cultured on polyorthoester fibers (5A) after three days in culture then, (5B) after an additional day, implanted in the omentum of an animal for seven days, demonstrating growth and vascularization.
Figure 5B:
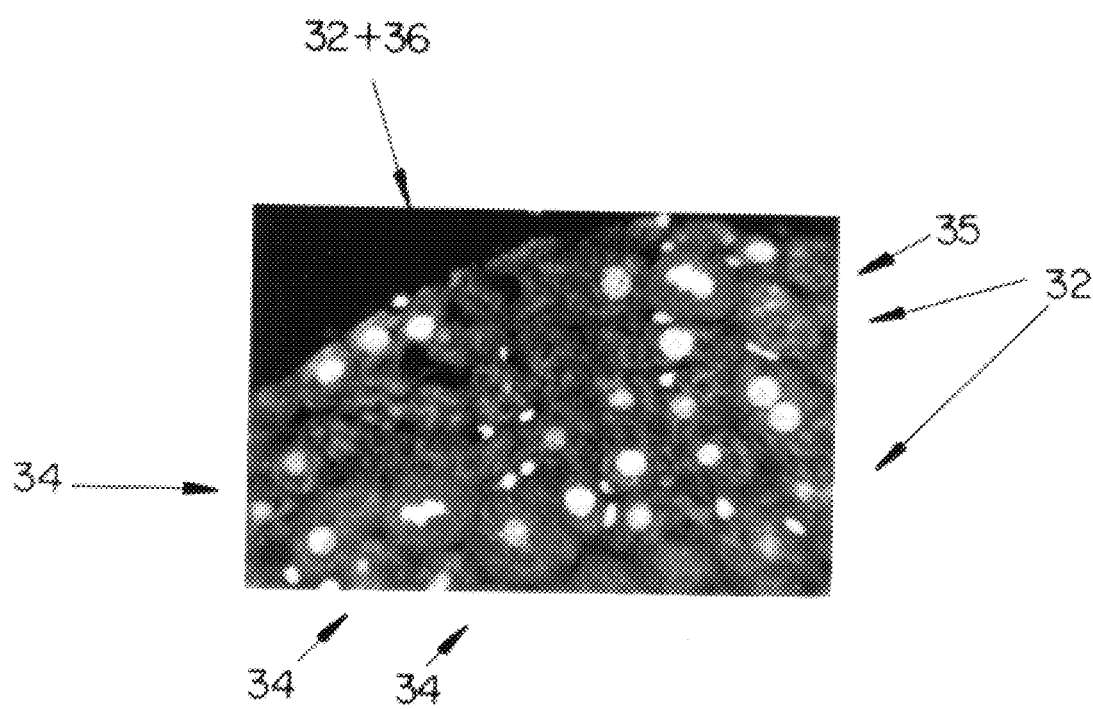

In a second successful example, fetal rat liver was minced, placed on branching fibers of polyorthoester, and cultured for 4 days. FIG. 5A is a photograph of the cultured cells after three days. The polymer plus cell combination was then implanted into the omentum of a three week old rat and a partial hepatectomy performed. The animal was sacrificed and studied 7 days later. Small clusters of hepatocytes 32 were seen among polymer fibers 35, as shown by the photograph of FIG. 5 B. There was blood vessel 34 ingrowth and a moderate inflammatory response. Bile canalicular membranes 36 were observed between adjacent hepatocytes. The hepatocytes were large, pale pink, and healthy in appearance.

Figure 6A:
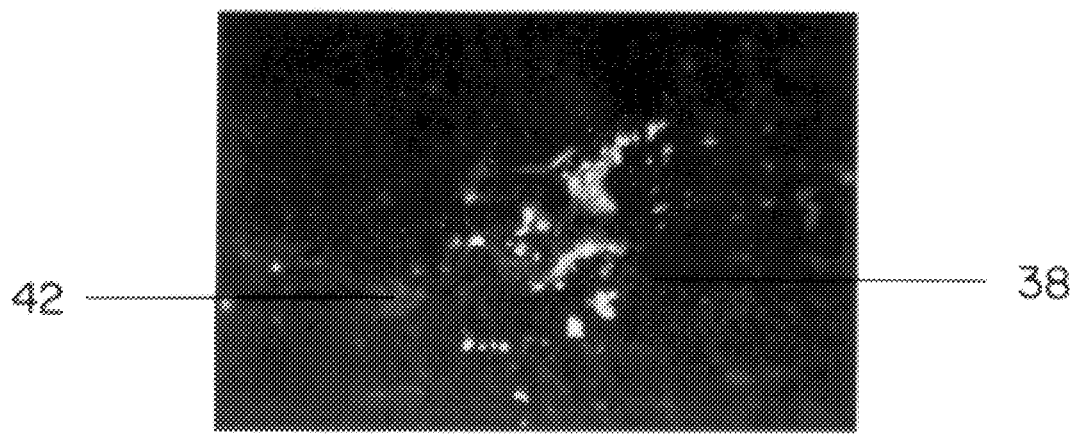
FIG. 6A and 6B are photographs of intestinal cells cultured on polymer fibers for four days (6A), then implanted in the omentum of an animal for seven days(6B), demonstrating growth and intrinsic organization of the cells.
Figure 6B:

In a third successful example of the present invention, intestinal cells were successfully cultured on polymer matrix and implanted in an aminal. Fetal rat intestine was minced, cultured 4 days on branching fibers of polyorthoester, and implanted in the omentum of a three week old rat. After 7 days, the rat was sacrificed. The successful growth of the cells 38 is demonstrated in the photograph of FIG. 6B The cells 38 are healthy in appearance, forming a distinct tubule 40 of cells on the polymer 42. Ingrowth of blood vessel 44 was also apparant.

If appropriate, immunosuppressant drugs may be injected or incorporated into the polymer structure. However, a limited inflammatory reaction to the implant may in fact be desirable to promote growth. This encourages a more normal healing response and may play a role in the "calling in" of new blood vessels.

The use of the donor's own cells or cells from which the lymphocytes have been removed prior to culturing is especially important in the culturing and implantation of intestinal cells. If the lymphocytes are not removed from the intestinal cells prior to implantation, the result can be "graft vs. host" disease. The present invention decreases this possibility since only the cells needed for function are placed on the polymers and implanted into the patient.

Figure 7:
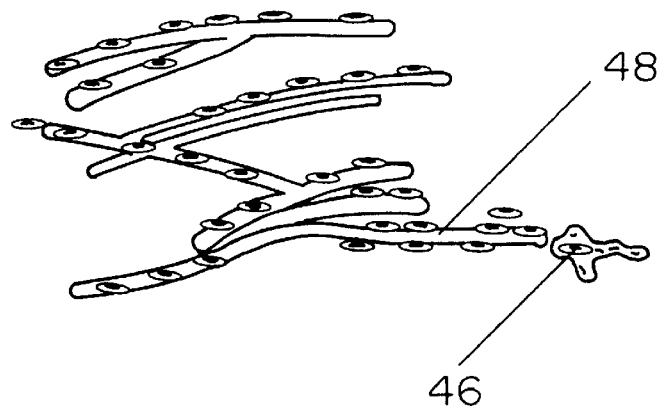
FIG. 7 is a plan drawing of polymer fibers embedded in Matrigel™ seeded with BAE cells.

The method of the present invention is highly versatile and useful both in vivo and in vitro. FIG. 7 is a drawing of BAE cells on polymer fibers, embedded in Matrigel™, demonstrating the usefulness of the method of the present invention in creating three-dimensional organ structures in vitro.

The criteria for successful growth and implantation is when the transplant demonstrates functional equivalency to the organ which it is replacing or supplementing. For example, a functional kidney would not necessarily have to manufacture renin as long as it functions as an effective dialysis apparatus, removing concentrated low molecular weight materials from the bloodstream. A functional liver may only need to produce proteins such as coagulation factors and excrete bile. For this purpose the liver transplant could be implanted in the omentum, the fatty, highly vasculated membrane adjacent to the small intestine. A functional intestine should be able to absorb sufficient nutrients to sustain life. This could be in the form of caloric solutions rather than normal "foodstuffs". "Secretory" organs in addition to a liver or a pancreas can be made by applying the same method of selecting secretory cells, constructing a matrix, culturing the cell on the matrix, and implanting the cell-matrix structure into an area which promotes vascularization of the cell-matrix structure.

Figure 8:
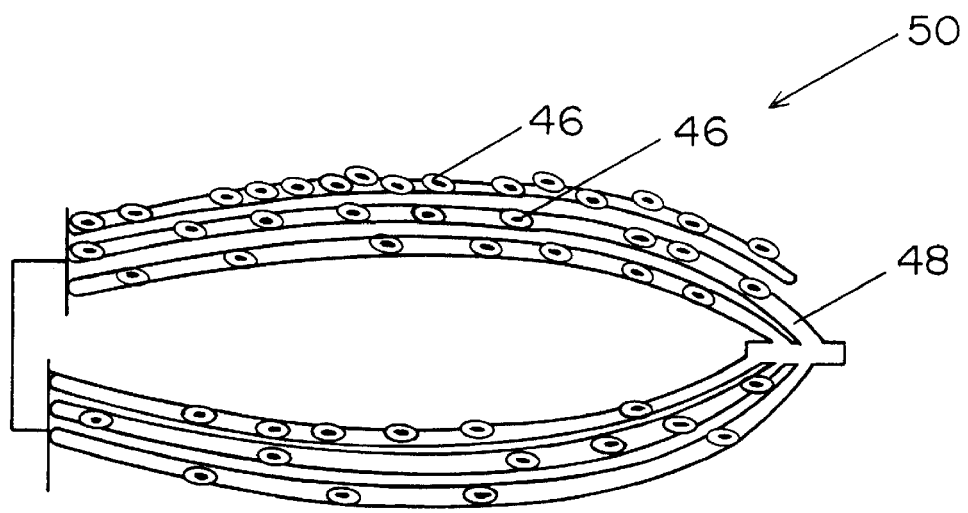
FIG. 8 is a plan drawing of long polymer fibers seeded with muscle cells.

As demonstrated in FIG. 8, "organs" other than secretory organs can be made using the method of the present invention. For example, muscle cells 46 may be seeded onto extended fibers 48. These long fibers can be used to form muscle segments, such as the structure 50 shown in FIG. 8.

Figure 9:
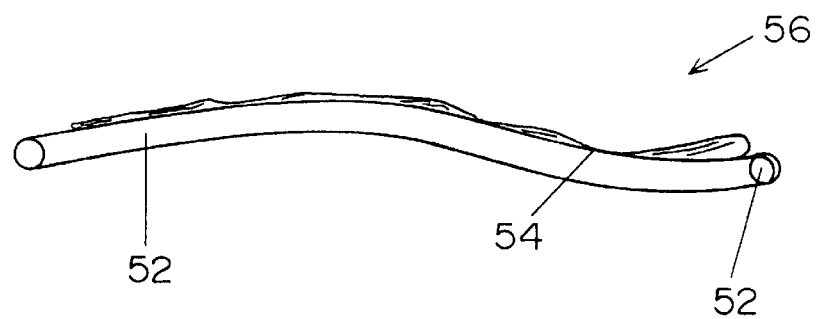
FIG. 9 is a perspective drawing of a bioabsorbable polymer fiber used for growth of nerve cells.

Nerves may also be constructed using long fibers 52 containing an appropriate nerve cell 54. Following growth of the nerve along the length of the fiber, the structure 56 is implanted at the appropriate location extending from a nerve source to the area in which nerve function is desired. Such a structure 56 is shown in FIG. 9.

Figure 10A:
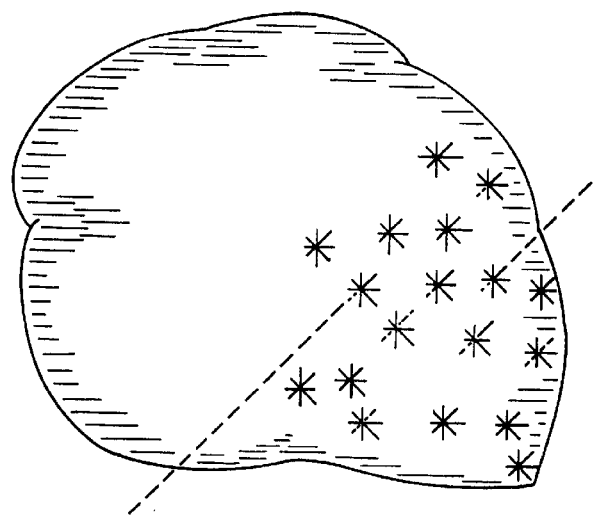
FIG. 10A is a plan drawing of polymer spicules seeded with heart muscle cells and implanted on the myocardium of the heart.
Figure 10B:
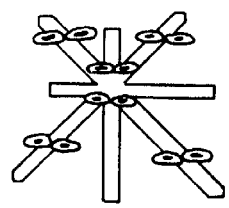
FIG. 10B is an enlarged plan view of a spicule, as shown in FIG. 10A.

As shown in FIG. 10A and FIG. 10B, the present invention can be utilized in patients suffering from cardiac myopathy. Muscle cells are grown on polymer spicules (FIG. 10B), which are then embedded on the surface of the heart itself (FIG. 10A). In accordance with the previously discussed principles, the damaged heart itself would not be replaced but new, strong muscle tissue would grow across the damaged area, beating in synchrony with the underlying tissue, and restoring some of the lost function and partially remodeling the scar tissue.

Although this invention has been described with reference to specific embodiments, variations and modifications of the method and means for constructing artificial organs by culturing cells on matrices having maximized surface area and exposure to the surrounding nutrient-containing environment will be apparent to those skilled in the art. Such modifications and variations are intended to come within the scope of the appended claims.

We claim:

1. A method for preparing a scaffold for preparing a cell-scaffold composition for growing cells in vitro to produce functional vascularized organ tissue in vivo comprising:

providing fibers made of a biocompatible, biodegradable, synthetic polymer, and forming the fibers into a fibrous three-dimensional scaffold composed of the fibers, wherein the fibers of the scaffold provide sufficient surface area to permit attachment in vitro of an amount of the cells effective to produce the functional vascularized organ tissue in vivo;

wherein the fibers of the scaffold are spaced apart such that the maximum distance over which diffusion of nutrients and gases must occur through a mass of cells attached to the fibers is between 200 and 300 microns; and wherein the diffusion provides free exchange of nutrients, gases and waste to and from the cells uniformly attached to the fibers of the scaffold and proliferating throughout the scaffold in an amount effective to maintain cell viability throughout the scaffold in the absence of vascularization.

2. The method of claim 1 further comprising:

b) providing a population of cells derived from a vascularized tissue, c) attaching the cells in vitro to the surface of the fibers of the scaffold uniformly throughout the scaffold; and d) growing the cells on the scaffold in a nutrient solution in vitro to form the cell-scaffold composition.

3. The method of claim 2 further comprising:

e) implanting the cell-scaffold composition in a host at a location having adequate vascularization to allow growth of blood vessels into the cell-scaffold composition.

4. The method of claim 3 further comprising implanting a matrix formed of a biodegradable polymer including growth factors into the host at the location where the cell-scaffold composition is to be implanted.

5. The method of claim 3 further comprising implanting additional cell-scaffold compositions having different cell populations.

6. The method of claim 2 further comprising removing lymphocytes from the cell population prior to attaching the cells to the scaffold.

7. The method of claim 3 further comprising selecting cells of a tissue type compatible with the host's cells.

8. The method of claim 2 further comprising incorporating growth factors into the cell-scaffold composition.

9. The method of claim 1 further comprising selecting the polymer from the group consisting of polyorthoesters, polyanhydrides, polyglycolic acid, and combinations thereof.

10. The method of claim 1 wherein the scaffold is configured as branched fibers of small diameter extending outwardly from a central stem.

11. The method of claim 2 further comprising selecting the cells from the group consisting of hepatocytes, bile duct cells, parathyroid cells, thyroid cells, cells of the adrenal-hypothalmic-pituitary axis, heart muscle cells, kidney epithelial cells, kidney tubular cells, kidney basement cells membrane cells, nerve cells, blood vessels cells, intestinal cells, cells forming bone, smooth muscle cells and skeletal muscle cells.

12. The method of claim 2 wherein the cells are hepatocytes and the biodegradable polymer is a polymer degrading by hydrolysis.

13. The method of claim 2 wherein the cells are pancreatic cells and the biodegradable polymer is a polymer degrading by hydrolysis.

14. The method of claim 2 wherein the cells are intestinal cells and the biodegradable polymer is a polymer degrading by hydrolysis.

15. The method of claim 9 wherein the polymer is overlaid with a material selected from the group consisting of collagen and basement membrane material.

16. The method of claim 2 further comprising incorporating compounds stimulating angiogenesis into the cell-scaffold composition.

17. The method of claim 2 further comprising incorporating immunomodulators into the cell-scaffold composition.

* * * * *

UNITED STATES PATENT AND TRADEMARK OFFICE
CERTIFICATE OF CORRECTION

PATENT NO. : 5,770,193
DATED : June 23, 1998
INVENTORS : Joseph P. Vacanti and Robert S. Langer It is certified that error appears in the above-identified patent and that said Letters Patent is hereby corrected as shown below:

On the title page, item [75]:
In the Inventors, Robert S. Langer is not from "Somerville, but is from --Newton--;

In col. 1, line 60, replace "transplantation. the" with --transplantation. In the--;

In col. 2, line 17, replace "Ingenious" with --ingenious--;

In col. 2, line 34, replace "form" with --from--;

In col. 3 line 7, replace "threedimensional" with --three-dimensional--;

In col. 4, line 14-16 replace "cells having formed bone," with --cells forming bone--;

In col. 5, line 67, replace "surfaces-so" with --surfaces so--; and

In col. 6, line 10, replace "onto" with --onto the --.

Signed and Sealed this

Tenth Day of April, 2001

*Attest:*

NICHOLAS P. GODICI

*Attesting Officer*   Acting Director of the United States Patent and Trademark Office